United States Patent [19]
Cornsweet et al.

[11] Patent Number: 5,410,376
[45] Date of Patent: Apr. 25, 1995

[54] EYE TRACKING METHOD AND APPARATUS

[75] Inventors: Tom N. Cornsweet, Irvine; Michael Rothberg, Foothill Ranch; Ross J. Beesmer, Irvine, all of Calif.

[73] Assignee: Pulse Medical Instruments, Rockville, Md.

[21] Appl. No.: 191,588

[22] Filed: Feb. 4, 1994

[51] Int. Cl.⁶ ............................................... A61B 3/14
[52] U.S. Cl. .................................... 351/210; 351/209; 351/221
[58] Field of Search ............... 351/200, 208, 209, 210, 351/221, 246; 354/62

[56] References Cited

U.S. PATENT DOCUMENTS

| | | | |
|---|---|---|---|
| 3,804,496 | 4/1974 | Crane et al. | 351/210 |
| 4,789,235 | 12/1988 | Borah et al. | 351/210 |
| 4,850,691 | 7/1989 | Gardner et al. | 351/221 |
| 4,854,329 | 8/1989 | Walruff | 128/745 |
| 5,090,799 | 2/1992 | Makino et al. | 351/221 |
| 5,196,872 | 3/1993 | Beesmer | 351/208 |

Primary Examiner—William L. Sikes
Assistant Examiner—Huy Mai
Attorney, Agent, or Firm—Whitham, Curtis, Whitham & McGinn

[57] ABSTRACT

An improved eye tracking system capable of accurately measuring fast eye movements, is controlled by a microprocessor and software to rapidly track a subject's eye movements. The hardware for the electro-optical tracking system includes a quadrant detector which detects the relative direction of movement of the subject's eye. The output of the quadrant detector is processed by the microprocessor under the control of three software subsystems. The first software subsystem is the servo tracking software which controls positioning motors that rapidly move a mirror mechanism which reflects light that forms an image of the subject's eye on the quadrant detector. The second software subsystem is the pupil recognition software which recognizes that an image of a pupil is present. The third software subsystem is the blink detection software which recognizes the presence of a blink and disables the servo tracking subsystem. These three software subsystems work together to insure accurate tracking of a subject's eye movements.

16 Claims, 11 Drawing Sheets

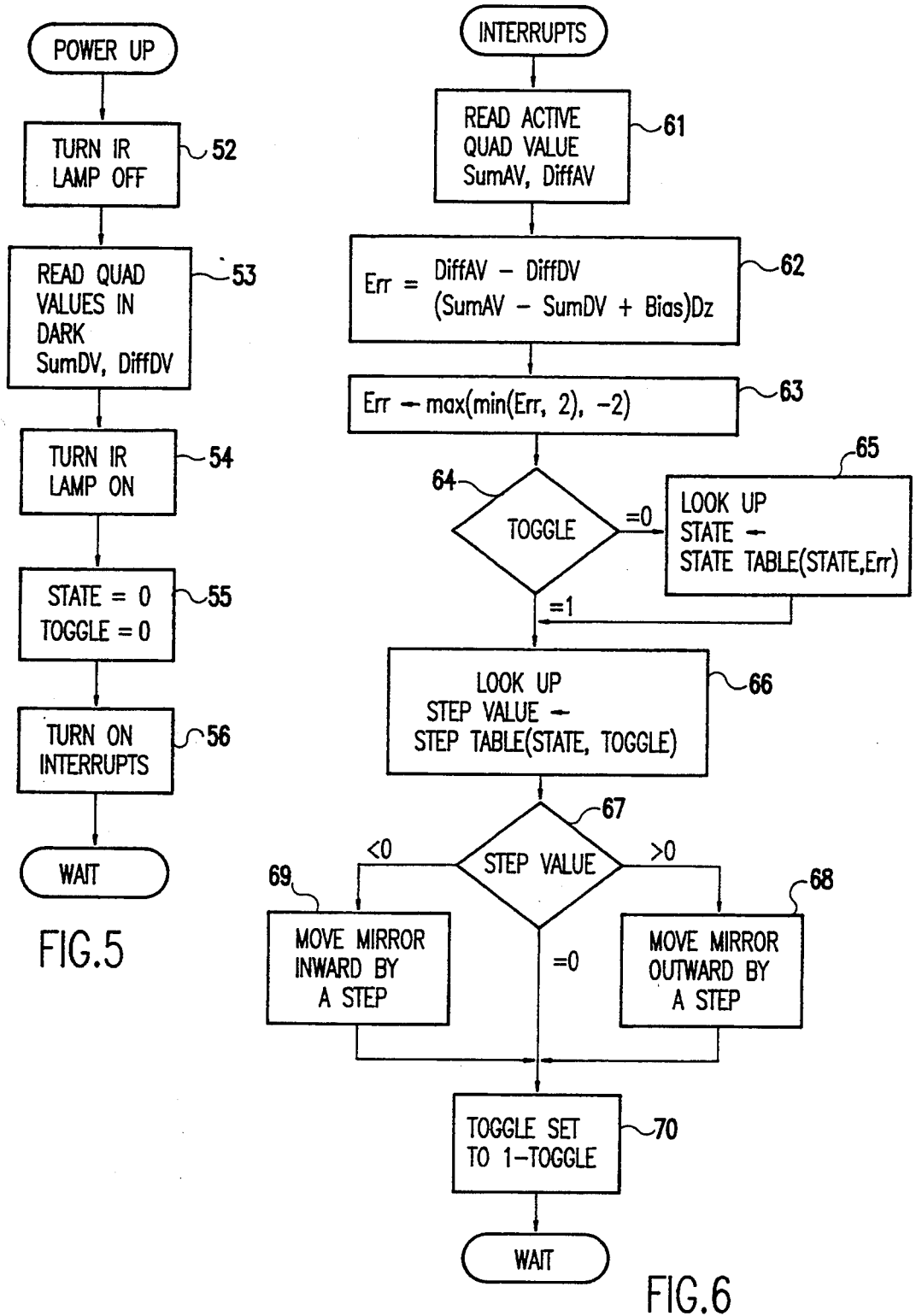

EYE TRACKING METHOD AND APPARATUS

BACKGROUND OF THE INVENTION

1. Field of the Invention

The present invention generally relates to eye tracking method and apparatus and, more particularly, to an improved eye tracking system having particular application for the measurement of saccadic eye movements.

2. Description of the Prior Art

An example of an ophthalmological instrument that implements an eye tracking mechanism for data acquisition is disclosed in U.S. Pat. No. 5,196,872 to Beesmer et al. This instrument requires an operator who, working with a subject, positions images of the subject's pupils on a display screen prior to performing a series of tests. During these tests, the subject's eyes remain relatively stationary, although there will be some small involuntary movement. The tracking system therefore needs to have only a limited response speed and, in fact, the response speed of the tracking system, incorporating as it does the video camera which images the subject's pupils, is limited by the video scanning rate of 60 Hz. This is quite adequate for the ophthalmological instrument disclosed in the Beesmer et al. patent; however, the response speed of that tracking system is not sufficient where fast eye movements are to be measured.

When a person looks from one place to another, the eyes undergo extremely fast rotations (up to 600° per second), called saccadic eye movements, or saccades. It is useful for some applications to track the eye even when it is moving at the very high speeds of saccadic eye movements. For example, if the eye is to be tracked to measure some property like pupil diameter as in the ophthalmological instrument disclosed in the Beesmer et al. patent, a saccade can cause loss of tracking. While there are some video-based instruments that purport to measure saccadic eye movements, what they in fact measure is the presence of a movement faster than they can track. When such a movement is detected, these instruments declare the movement a saccade, and from this information, simply estimate the number of saccadic movements and when they occurred. If it is desirable to know where a person's eye is pointed right after a saccade, e.g., where the person is looking, the inability to track the eye at such high speeds results in loss of this information. It may also be desirable to know about the properties of the saccade itself, as in cases where the saccadic velocity is a significant variable to measure.

Because saccades are so quick (even a large one only lasts 50 or so milliseconds), they cannot be measured accurately unless the position of the eye is sampled at a high rate. Ordinary video rates (i.e., 17 or 34 msec between samples) do not give accurate readings of onset time, velocity, amplitude, shape, etc. Some special video systems having frame rates up to 400 Hz have high enough sampling rates, but these systems are very expensive and require high light levels that are not compatible with tracking the eyes. Therefore, it is desirable to sense eye positions with a photodetector which may be sampled at very high rates yet requires relatively low light levels so as to be compatible with an ophthalmological instrument.

SUMMARY OF THE INVENTION

It is therefore an object of the present invention to provide an improved eye tracking system which is capable of accurately measuring fast eye movements.

According to the invention, there is provided an electro-optical eye tracking system controlled by a microprocessor and software to rapidly track a subject's eye movements. The hardware for the electro-optical tracking system includes a four quadrant detector which detects the relative direction of movement of the subject's eye. The output of the four quadrant detector is processed by the microprocessor under the control of three software subsystems. The first software subsystem is the servo tracking software which controls positioning motors that rapidly move a mirror mechanism which reflects light that forms an image of the subject's eye on the four quadrant detector. The second software subsystem is the pupil recognition software which recognizes that an image of a pupil has been acquired by the electro-optical system. The third software subsystem is the blink detection software which recognizes the onset of a blink and disables the servo tracking subsystem. These three software subsystems work together to insure accurate tracking of a subject's eye movements.

The electro-optical eye tracking system may be combined with an imaging system which includes a video camera that forms an image of the subject's pupil. Such an imaging system may be used to perform a variety of ophthalmological tests for diagnostic and screening purposes.

BRIEF DESCRIPTION OF THE DRAWINGS

The foregoing and other objects, aspects and advantages will be better understood from the following detailed description of a preferred embodiment of the invention with reference to the drawings, in which:

FIG. 1A is a plan view showing the arrangement of the four quadrant detector employed in the eye tracking system shown in FIG. 1;

FIG. 5 is a flow diagram showing the logic of the software that controls the microprocessor of the system shown in FIG. 4 at power up;

FIG. 6 is a flow diagram showing the logic of the software subsystem that controls the microprocessor of the system to actively track eye movement and generate a measure of saccadic eye movement;

DETAILED DESCRIPTION OF A PREFERRED EMBODIMENT OF THE INVENTION

Figure 1:
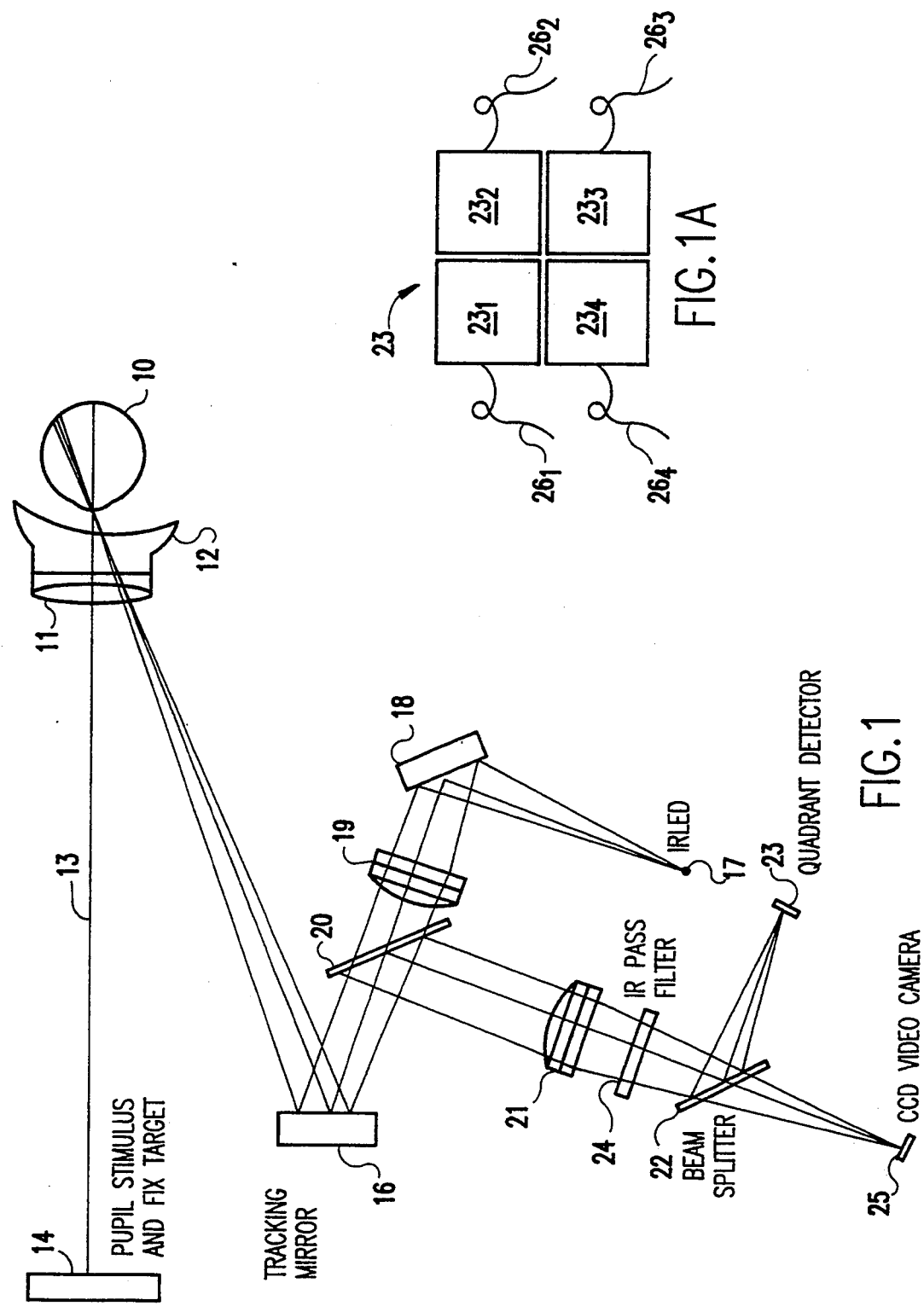
FIG. 1 is a schematic diagram showing the basic components of the eye tracking system according to a preferred embodiment of the invention.

Referring now to the drawings, and more particularly to FIG. 1, there is shown in schematic form the basic components of the eye tracking system according to a preferred embodiment of the invention. The subject's eye 10 is positioned relative to an eyepiece 11 having an eyecup 12 so that initially the subject's gaze is aligned along center line 13 toward a pupil stimulus and fixation target 14.

The tracking system itself includes a tracking mirror 16 which pivots about two perpendicular axes. The pupil of the subject's eye is illuminated by an infrared (IR) light emitting diode (LED) 17. The light from the LED 17 is reflected by a fixed mirror 18 through an imaging lens 19 and beam splitter 20 to tracking mirror 16. The IR light is reflected by the tracking mirror 16 through the eyepiece 11 to the subject's eye 10, where it forms an image of IR LED 17 that is much smaller than the smallest that the pupil ever becomes. The light thus passes through the pupil and falls on the retina, where it is backscattered.

Backscattered light that exits the eye through the pupil is reflected by the mirror 16 to beam splitter 20 which reflects the light through imaging lens 21 and IR-pass filter 24 to a second beam splitter 22. Part of the IR light is reflected by the beam splitter 22 to a four quadrant detector 23, shown in more detail in FIG. 1A, and part of the IR light is passed by the beam splitter 22 to a video camera 25, typically in the form of a charge coupled device (CCD).

In an application of a preferred embodiment of the invention, the camera 24 is used for making pupil diameter measurements during a part of a test procedure. The tracking system according to the invention is independent of the camera and pupil diameter measuring system and, therefore, that system will not be described in detail here. For a description of a suitable system for measuring pupil diameter, see U.S. Pat. No. 5,196,872 to Beesmer et al. The camera video can also be used to correct certain kinds of errors, particularly those associated with the use of stepper motors as positioning motors for the tracking mirror. For example, when the eye moves slowly and smoothly (i.e., "pursuit movement"), the motor position of course consists of a series of steps, which, if plotted, make it look like the eye is stepping instead of moving smoothly. However, for these slow movements, the video rate is fast enough that motion of the image across the camera can be measured between motor steps. The tracking mirror tries to null the movements of the image of the eye, but the tracking mirror being driven by a stepper motor, moves in steps; however, if the eye is moving smoothly, its image will move smoothly between steps. Thus, by measuring the displacement of the video and adding it to the motor position display, a better representation of what the eye is actually doing is achieved.

The tracking system according to the invention uses a four quadrant detector 23, instead of the camera 25. A plan view of the four quadrant detector 23 is shown in FIG. 1A and comprises IR detectors $23_1$, $23_2$, $23_3$, and $23_4$, one for each of first, second, third, and fourth quadrants of an image plane onto which an image of the subject's pupil is projected by the beam splitter 22. Wires $26_1$, $26_2$, $26_3$, and $26_4$, respectively connected to IR detectors $23_1$, $23_2$, $23_3$, and $23_4$, carry analog signals corresponding to the amount of IR light falling on the corresponding detector. These analog signals are combined and digitized for processing by a microprocessor, as described in more detail with reference to FIG. 4 below.

Figure 2:
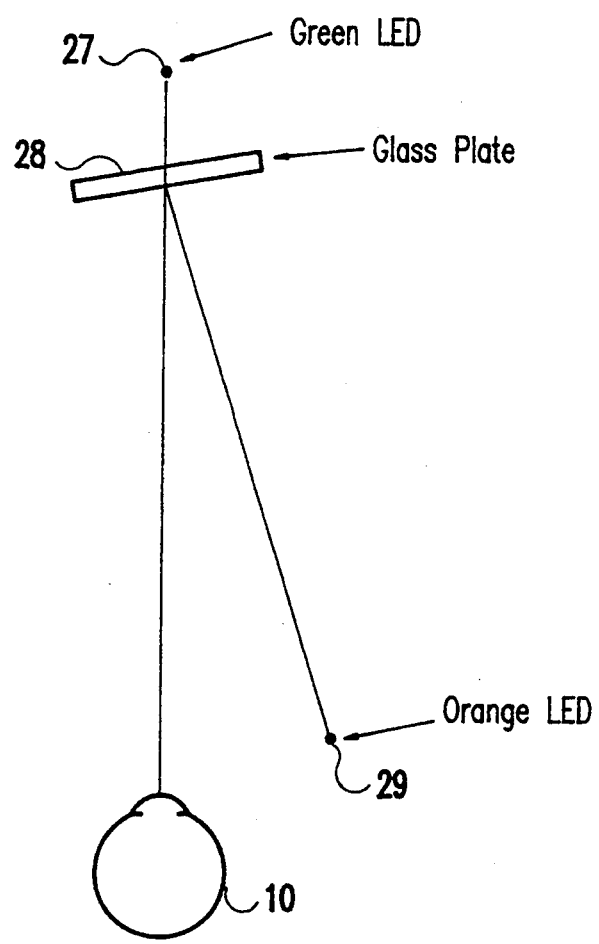
FIG. 2 is a simplified schematic diagram showing the fixation lamps used to initially position and align a subject's eye with respect to the measuring optics.

With reference now to FIG. 2, there is schematically shown the fixation lamps which assist the subject in aligning their eye with the optical axis of the system. The green LED 27, which is part of the fixation and stimulus target 14, is viewed directly through the pane of glass 28. The orange LED 29 is viewed by reflection from the glass 28. The optical distance from the eye to the orange LED 29 is about twice as great as the optical distance from the eye 10 to the green LED 27. Therefore, moving the head horizontally or vertically produces motion parallax so that one light appears to move with respect to the other.

The subject looks through the eyepiece 11 while the eye is a few inches away from the instrument incorporating the system according to the invention. In this position, the subject sees a small orange light and a small green light generated respectively by LEDs 29 and 27. The subject then moves sideways and up and down until the two lights appear superimposed. The subject then moves up to rest against the rubber eyecup 12 while maintaining the superimposition of the two lights. This places the eye on the optical axis of the measuring optics.

Figure 3:
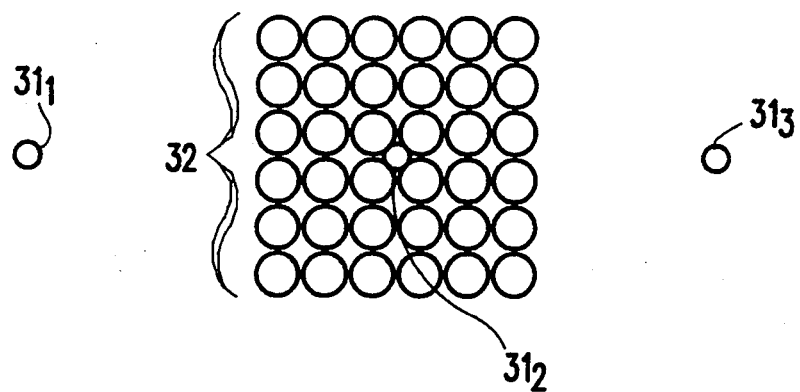
FIG. 3 is a simplified schematic diagram showing the pattern of the pupil stimulus lights used in an application of the preferred embodiment of the invention.

FIG. 3 shows the pattern for the stimulus lights as used in a specific application of the preferred embodiment of the invention. These lights are embedded in the stimulus target 14. There are, in addition to LEDs 27 and 29 (not shown in this figure), two arrays of LEDs. The first array is a linear array comprising LEDs $31_1$, $31_2$ and $31_3$ positioned along a horizontal axis. LEDs $31_1$ and $31_3$ are, respectively, at distances from the center which subtend, at the eye, approximately 10° of arc to the left and right of center. LED $31_2$ is located directly on center and, in the preferred embodiment, is the same as LED 27. The second array is a matrix of larger LEDs 32, here shown as a 6×6 matrix array. This matrix array is shown symmetrically arranged about the center of the stimulus target 14.

The matrix array of LEDs 32 is used to stimulate the pupil while pupil diameter measurements are made. This type of measurement is made using the camera 24. For a description of this pupil measurement system, see U.S. Pat. No. 5,196,872 to Beesmer et al. The eye tracking system according to the present invention works in cooperation with the LEDs $31_1$, $31_2$ and $31_3$ which are controlled to turn on and off in a predetermined sequence to stimulate saccadic movements in the subject's eye.

Figure 4:
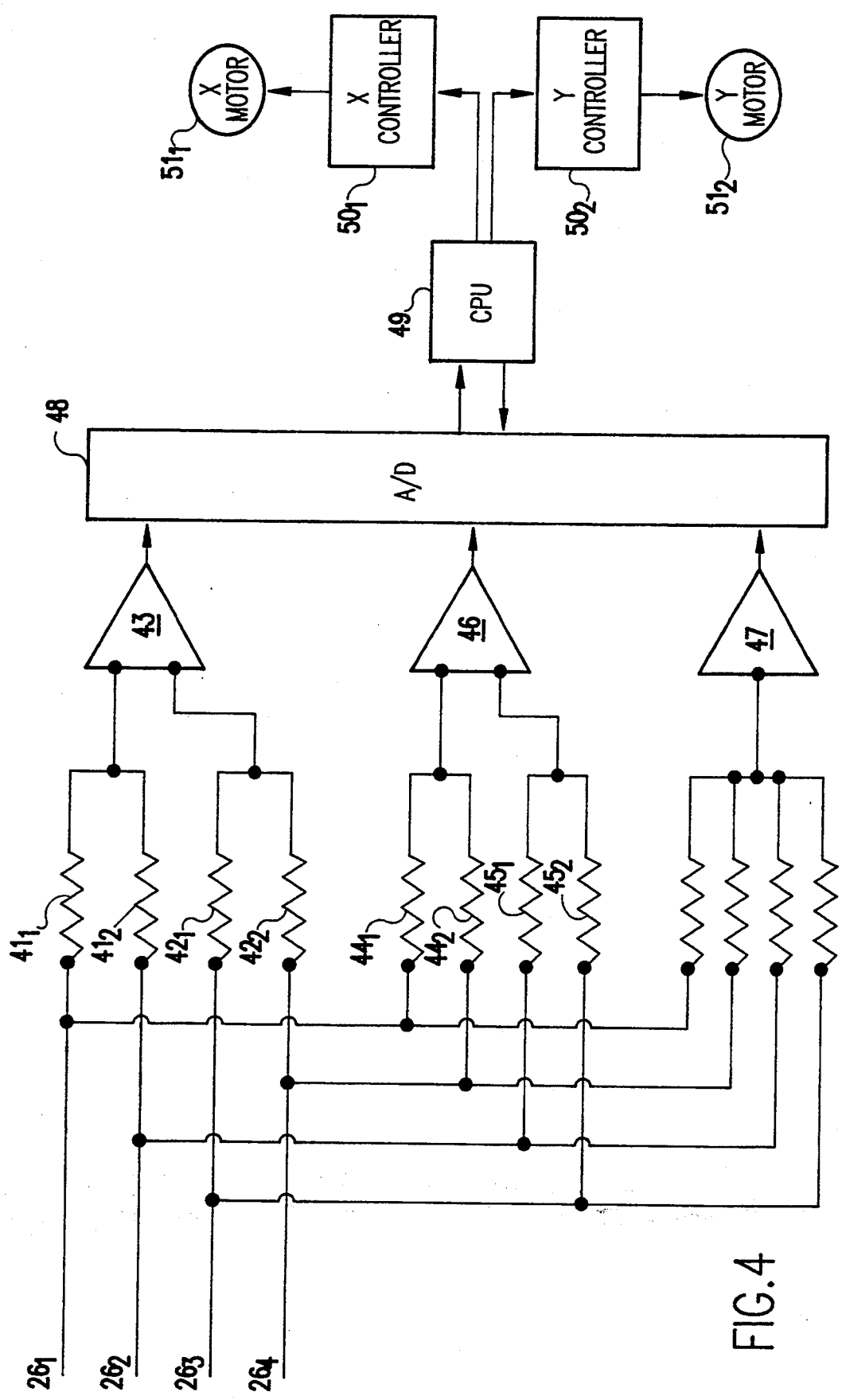
FIG. 4 is a block diagram showing the electromechanical components of the eye tracking system.

FIG. 4 shows a block diagram of the analog electronic components of the eye tracking system according to the invention. As mentioned with reference to FIG. 1A, the outputs on wires $26_1$, $26_2$, $26_3$, and $26_4$, respectively connected to IR detectors $23_1$, $23_2$, $23_3$, and $23_4$, are analog signals corresponding to the amount of IR light falling on the corresponding detector. Each quadrant detector output is connected to amplifiers through a resistor. More particularly, wires $26_1$ and $26_2$ are connected to resistors $41_1$ and $41_2$, respectively, which are in turn connected to the sum, or non-inverting, input of "vertical" amplifier 43. These resistors cause their outputs to add at the plus, or non-inverting, input of the "vertical" amplifier 43. Wires 26₃ and 26₄ are connected to resistors 42₁ and 42₂, respectively, which are in turn connected to the minus, or inverting, input of "vertical" amplifier 43. These resistors cause their outputs add at the minus, or inverting, side of the "vertical" amplifier 43. Therefore, if the image of the pupil is above the horizontal center line of the four quadrant detector, the plus voltage will be proportionally bigger than the minus voltage. Since amplifier 43 outputs the difference, it is a bipolar measure of the vertical position error of the tracking servo.

Similarly, the same quadrant detectors are connected to a different set of resistors in a corresponding way to give the horizontal error signal. Specifically, wires 26₁ and 26₄ are connected via resistors 44₁ and 44₂ to the plus, or non-inverting, input of "horizontal" amplifier 46, and wires 26₂ and 26₃ are connected via resistors 45₁ and 45₂ to the minus, or inverting, input of the "horizontal" amplifier 46. The output of amplifier 46 indicates the degree to which the pupil image is decentered horizontally. Finally, the wires 26₁, 26₂, 26₃, and 26₄ are connected to a third amplifier 47 to produce a signal that is the sum of the active IR light on the four quadrant detector 24.

Each of the signals from amplifiers 43, 46 and 47 are digitized by a multiplexed analog-to-digital (A/D) converter 48. This converter is controlled by a microprocessor 49 which receives the digitized outputs for processing. After performing the processing on the digitized signals, the microprocessor 49 generates stepper outputs representing the vertical axis (X) displacement and horizontal axis (Y) displacement of the tracking mirror 16. These stepper outputs are supplied to X controller 50₁ and Y controller 50₂, which respectively control stepper positioning motors 51₁ and 51₂. The stepper motors 51₁ and 51₂ pivot the tracking mirror 16 in the proper directions to track the subject's eye movement. While in the preferred embodiment of the invention, the motors 51₁ and 51₂ are stepper motors, other motors, such as voice coil motors, could be used.

The software portion of the eye tracker can be logically divided into three portions, or subsystems. These subsystems are the tracking servo loop, pupil recognition and blink detection. The most important of these is the tracking servo loop which can function independently of the other two subsystems; however, as will be appreciated from the following description, the pupil recognition and blink detection subsystems provide useful augmentation to the function of the tracking servo loop subsystem.

It is the function of the tracking servo loop subsystem to give commands to the motors that control the tracking mirror in such a way that the backlighted image of the pupil will be centered as much as possible on the four quadrant detector. In principle, the feedback loop that performs this function is very simple. The image of the pupil on the four quadrant detector produces an error signal, which is used to determine how and when to move the motors. Moving the motors causes the image of the pupil on the four quadrant detector to shift, which, in turn, causes a change in the error signal. Moving the mirror also causes the input light to remain centered in the pupil. It is clear from this brief description that the role of the microprocessor in the loop is to always move the motors to cause a decrease in the error signal.

One inherent problem with servo systems is to balance the conflicting requirements of the system to respond to fast changes and for the system to be stable. If the target being tracked, in this case the eye, moves off center very rapidly in some direction, then the tracker must move in the same direction at the same speed. Furthermore, in any real system, causality dictates that there will always be a delay between when the target changes its speed and when the tracker senses this change and can respond with a change in its own speed. Hence, in order for the tracker to "catch up" to the target, it must actually travel faster than the target for some period. If the "gain" on the tracking system is defined as the distance the tracker moves in response to a move of the target divided by the distance the target actually moved, then the gain of the tracker that is able to catch a moving target for some period during its travel must be greater than one. However, according to the feedback control theory, any system with a feedback gain greater than one is inherently unstable. In other words, if the eye tracker were to always have a gain of greater than one, there would always be situations in which the eye could be stationary but the tracker keeps moving back and forward, indefinitely.

The way to solve this problem is to change the gain of the system with changing needs. The larger the distance the pupil is from the tracker's current location, the more unbalanced the light falling on the four quadrant detector and hence the larger the error signal. If large error signals produce fast movements of the tracker and smaller error signals produce slow movements of the tracker, the servo system is then both fast and stable.

The following description is for a specific implementation of the eye tracker using stepper motors. In this configuration, the microprocessor can command the motors that drive the tracking mirror to move the mirror up or down and to the right or to the left. The actual distance the mirror moves with each command is determined by the physical characteristics of the mirror mounting assembly and the motors themselves. This distance, which is fixed and not under microprocessor control, is called a "step". Since the mirror can only be moved in discrete units of distance, the only way to change the mirror's speed, is to change the number of motor steps per unit of time. Obviously, if linear motors were used, the speed and distance of travel could be continuously controlled. In theory, for the implementation using stepper motors, the tracking microprocessor need only monitor the error signal coming from the four quadrant detector and, when this error is bigger than one motor step, step the motor once. Thus, increases in the target speed will automatically produce an increase in error signal and a corresponding increase in motor step rate. The advantage of this approach is a continuously varying step rate that automatically adapts to changes in target speed. However, in this application, an asynchronous stepper motor controller has several disadvantages. First, the irregularity of the motor's activity makes storage of the motor step chronology (which is needed to reconstruct the eye's movements) very difficult. Second, calculations on irregularly sampled data are generally more complicated than on data sampled with fixed time intervals. Third, implementation of an asynchronous feedback loop would require the full attention of the microprocessor, prohibiting it from performing other tasks simultaneously.

With these limitations in mind, the best way to control the stepper motor is to set up a fixed rate clock (in the specific example, this clock is set to 900 Hz) and, on each tick of the clock, step the motor in one direction or the other or do not step the motor. By using this method, at most two bits per clock are required to save the motor step chronology. Furthermore, the interval between motor steps is always a fixed multiple of the clock period, simplifying eye position calculations. Finally, if the clock drives a microprocessor interrupt, then the portion of the time the microprocessor spends controlling the motors can be limited to a small interval following each clock tick, allowing servoing to take place as a "background" task while the microprocessor performs some other task in the foreground, which in a specific application of the invention involves controlling eye test timing and stimulus lights.

What now remains is how the microprocessor translates a given quadrant detector error into a particular motor speed. Since the frequency of the servo clock is fixed, any step rate of the motors must be the clock rate divided by an integer. For example, if the servo clock frequency is ServoRate, then one possibility for the step rates could be 0, ½ServoRate, and ServoRate. Then, the range of error values can be divided into three ranges and each assigned to a step rate. A step rate of 0 is chosen for a quadrant detector error value less than a predetermined value, referred to as DeadZone, and produces no motor activity. Given the value DeadZone, the following assignments can be made:

| If Quad Error is | Then Step Rate should be |
| --- | --- |
| less than DeadZone | 0 |
| less than 2 × DeadZone | ½ServoRate |
| greater than 2 × DeadZone | ServoRate |

Finally, there is one additional factor that complicates the servo algorithm. Every stepper motor has a maximum step rate at which it can be driven without losing steps. This rate is determined by the application in conjunction with the characteristics of the motor itself. Every stepper motor also has a stop-start rate, which is defined as the fastest the motor can be driven starting from a standstill and returning to a standstill without losing steps. In general, these rates are not equal. For the stepper motors in used in a specific implementation, the maximum step rate is greater than 1000 steps/second and the stop-start rate is about 600 steps/second. If a motor speed faster than the start-stop rate of the motor is required, then the motor must be "ramped up" to that speed and "ramped down" from that speed; that is, start out at a speed below the stop-start rate and gradually increase the step rate until the desired speed is reached. Thus, for the specific example, for the motors to run at a maximum step rate of 900 steps/second, one additional point (besides 0 and 900) was provided, namely 450 steps/second. However, the ramp could be implemented with how ever many points it needs to reach any speed up to the maximum step rate.

Turning now to FIG. 5, there is shown the flow diagram for the initialization process at power up. The outputs of the vertical, horizontal and sum amplifiers 43, 46 and 47 are initially measured with the IR LED 17 turned off. The microprocessor 49 first turns the IR LED 17 off in function block 52 and then reads the values from A/D converter 48 in function block 53. These values, referred to as DiffDV and SumDV, are values output when the IR LED 17 is turned off corresponding to a reference noise level. The IR LED 17 is then turned on in function block 54, and the state is set to "0" and the toggle is set to "0" in function block 55 according to the Step Table shown below:

STEP TABLE

|  |  | Toggle | |
| --- | --- | --- | --- |
|  |  | 0 | 1 |
| State | −3 | −1 | −1 |
|  | −2 | −1 | 0 |
|  | −1 | 0 | −1 |
|  | 0 | 0 | 0 |
|  | 1 | 0 | 1 |
|  | 2 | 1 | 0 |
|  | 3 | 1 | 1 |

Then in function block 56, the interrupts are turned on. That is, a hardware time is programmed by the computer to generate a software interrupt at a fixed rate. In function block 56, the hardware timer is programmed to generate interrupts at a rate of 900 per second and started. At the same time, the microprocessor's interrupt, corresponding to the hardware timer's interrupt request line, is unmasked, allowing it to respond to the interrupt signal sent by the hardware timer. At this point, the microprocessor has initialized the system and waits for an interrupt which begins the servo loop.

The technique used here to implement the servo loop is called a state machine. As such, the servo loop will always be in one and only one state. In this instance, the servo loop can take on one of fourteen possible states, which are determined by two state variables; i.e., STATE and TOGGLE. STATE can take on the seven values labelled "−3" to "3", and TOGGLE can independently take on the two values labelled "0" and "1". Both of these variables are initialized to the value "0" in block 55.

The steps in FIG. 5 take place prior to starting of the feedback loop. The IR lamp is turned off, and the Dark Values (DVs) of the quadrant detector signals are read and saved. These Dvs are defined as follows:

SumDV—The summation of the values from all four quadrants.

HDiffDV—Horizontal difference—The value from left half of detector minus value from right half of detector.

VDiffDV—Vertical difference—The value from top half of detector minus value from bottom half of detector.

DiffDV—The generic name for either HDiffDV or VDiffDV. This saves in duplication in the description of the servo algorithm, since the same procedure is applied to both independently.

Once these values have been obtained, the IR light is turned on and the interrupt clock started with the interrupts enabled. This begins the feedback loop described in FIG. 6, infra. In addition, the values SumAV and DiffAV (AV for Active Value) are analogous to their Dark Value counterparts but are continually updated while the servos are on at the time of each interrupt (i.e., 900 times per second).

In FIG. 6 there is shown the flow diagram for the actual eye tracking procedure which begins when the microprocessor 49 receives an interrupt. In function block 61, the microprocessor 49 reads the active values SumAV and DiffAV which are used in function block 62 to compute an error value Err according to the following equation:

$$Err = \frac{DiffAV - DiffDV}{(SumAV - SumDV + \text{Bias})Dz}.$$

The calculation performed in function block 62 converts quadrant detector values, as defined above, into the servo error signal. DZ is the dead zone value, and Bias is a constant whose value is determined such that the servos do not oscillate with small pupils. This value, Err, is truncated by the function in $$Err \leftarrow max(min(Err,2),-2).$$

The equation solved in function block 63 limits the error signal to the domain of the lookup table, which in the case described is from −2 to 2. Any error values outside this range are truncated. Note, max(a,b) returns the larger of the two values a and b, and min(a,b) returns the smaller of the two values a and b. In decision block 64, a determination is made as to whether the toggle according to the Step Table above is a "0" or a "1". If a "0", then in function block 65 the state value is read out of the State Table below:

STATE TABLE

|       |    | −2 | −1 | 0  | 1  | 2  |
|-------|----|----|----|----|----|----|
|       |    |    |    | Err |    |    |
|       | −3 | −3 | −1 | −1 | −1 | −1 |
|       | −2 | −3 | −2 | 0  | 0  | 0  |
|       | −1 | −3 | −1 | 0  | 0  | 0  |
| State | 0  | −2 | −2 | 0  | 2  | 2  |
|       | 1  | 0  | 0  | 0  | 1  | 3  |
|       | 2  | 0  | 0  | 0  | 2  | 3  |
|       | 3  | 1  | 1  | 1  | 1  | 3  |

After looking up the state value in the State Table above or if the toggle is a "1", then the microprocessor 49 looks up the step value in the Step Table in function block 66. The read out step value is tested in decision block 67 to determine if it is positive (i.e., >0), negative (i.e., <0) or equal to zero. If positive, the tracking mirror 16 is moved outward by a step in function block 68, but if negative, the tracking mirror 16 is moved inward by a step in function block 69. Of course, if the step value is equal to zero, the tracking mirror 16 is not moved. Once the mirror operation has been performed, the toggle is set to 1-toggle in function block 70, and the microprocessor 49 then waits for the next interrupt.

Every time an interrupt occurs (which is about every 1.1 ms), the operations in FIG. 6 are performed. These operations fall into two categories; i.e., determining the next state for the servo loop and performing a motor action. For the variable TOGGLE, this means toggling to its alternate value by the operation in block 70. For the variable STATE, things are a little more complicated. First, the current values of the quadrant detector outputs are read in function block 61, and then these values are used in function block 62 to compute a new value for the error signal, Err. In function block 63, the value Err is rounded to the nearest integer value and clipped to the range of the variable STATE. After computing a new value for Err, if TOGGLE is equal to "0", then Err's new value and the current value of STATE are used as indices in the State Table to lookup a new value for STATE. If TOGGLE equals "1", this lookup operation is skipped, and the value of STATE remains unchanged.

The stepper motor action can take one of only three actions: do nothing, step in one step, or step out one step. These actions are represented in the Step Table by the values 0, −1, and 1, respectively. One of the motor actions is taken each interrupt, and this action is determined by the Step Table using the current state, as defined by current value of the variables STATE and TOGGLE.

The second subsystem performs the pupil recognition. As mentioned, the pupil recognition system is not necessary for tracking; however, it does help in initial alignment if no operator is present to look at pupil images. When a subject puts his or her eye up to the eyepiece 12 of the instrument and the IR light from IR LED 17 enters the subject's pupil, a backlighted image of the subject's pupil is formed on the CCD camera 25, as shown in FIG. 1. This image appears as a bright, evenly illuminated circular disk surrounded by a dark background. Generally, no other features will be visible, except possibly a small reflection off the subject's cornea. If, however, the IR light misses the subject's pupil and projects onto some other feature, such as the iris or eyelid, the camera will see a blurry disk of light. This disk, unlike the backlighted pupil image, will be brightest in the middle and gradually become dimmer with increasing distance from the center. Also, the size of this blurry disk, unlike the size of the pupil disk, depends on the size of the IR light source, which does not change. The blurry disk, however, may become slightly larger when the IR light source becomes brighter, depending upon what feature it is imaged upon. The size of the pupil disk is assumed to be independent of IR intensity and proportional only to the subject's pupil size.

The pupil recognition subsystem consists of two independent "diameter" measurement processes. Each process finds the length of the longest horizontal segment that has a video brightness signal above the corresponding threshold level set for each process. These two measurements are made for each video field and passed on to the computer. The threshold of one of the "diameter" processes is kept at a fixed level, and its output value is used by this and the data collecting part of the instrument as the pupil diameter. The other diameter measurement process is used only by this subsystem and is multiplexed between two values based on the intensity of the pupil image.

Figure 7:
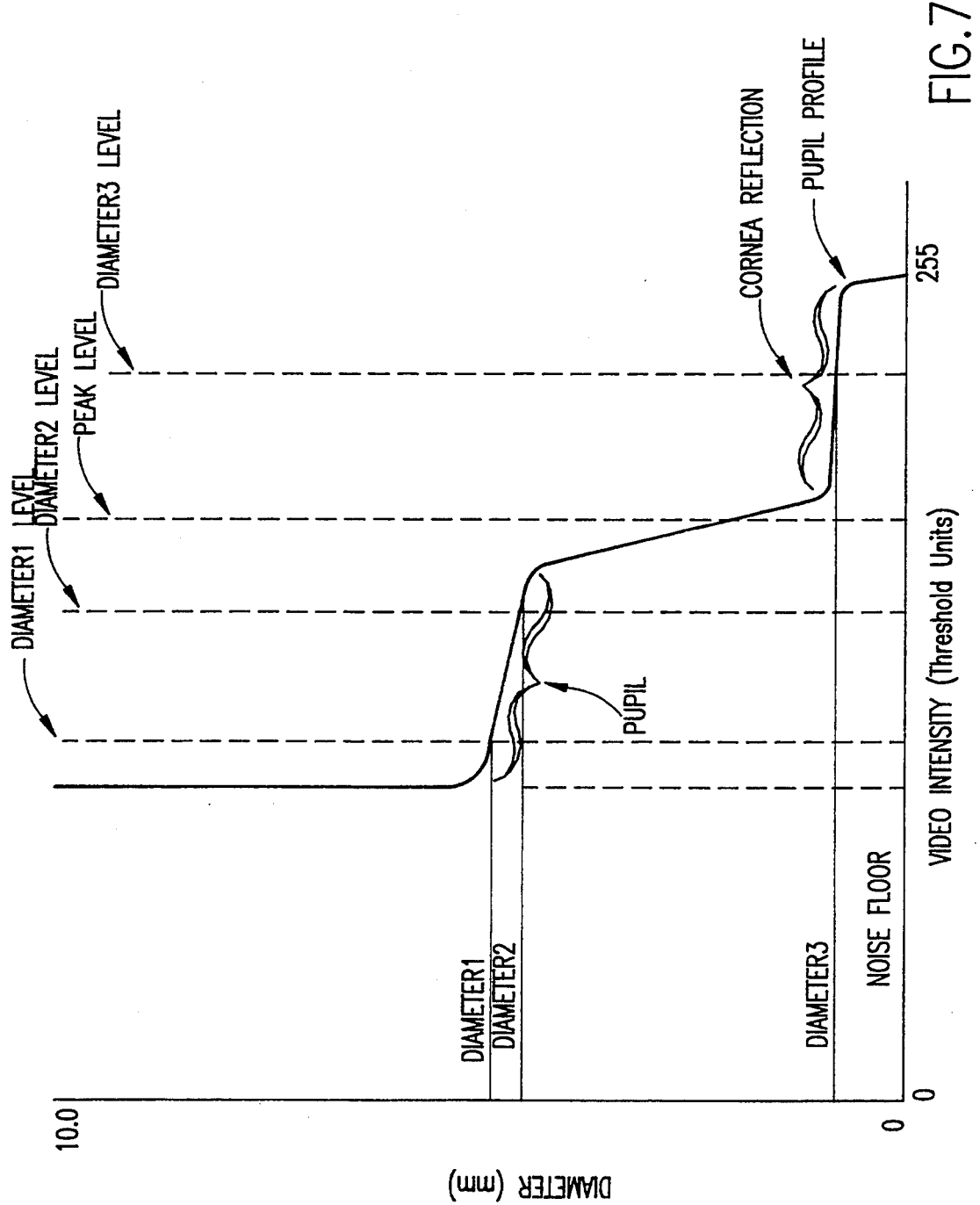
FIG. 7 is a graph showing the relation of the measurements made in the performance of the process of pupil identification.

The objective of the pupil recognition subsystem is to determine when there is a genuine pupil image on the camera 25 and when there is not. The subsystem should indicate that a pupil is not present when the screen is blank, as is true when there is no subject in the instrument, and also under the much more difficult condition of the having a blurry disk on the screen perhaps larger than the smallest pupil to be recognized. With reference to FIG. 7, the basic concept and rules implemented by the software are as follows:

PUPILPRESENT is the Boolean value that is the sole output of the pupil recognition subsystem. True means the camera sees a valid pupil image.

PEAKLEVEL is the highest video signal out of the camera after it has been low-pass filtered. After this signal is digitized and passed to the microprocessor (at a rate of sixty times per second or 60 Hz), it is then converted to threshold units by the software. This conversion results in a value that, when set in a threshold digital-to-analog (D/A) converter produces a voltage equal to the original voltage out of the low pass filter. If there is nothing blocking the eyepiece of the instrument, the value returned will be the dark level of the camera. Normally, little or no room light will enter the instrument. If the camera is looking at a pupil disk, then the value returned is the intensity of the pupil image, which, except for a corneal reflection peak, will be the brightest object. Generally, there will not be a corneal reflection peak (which rides on top of the pupil disk), but even if one does appear, its diameter is small enough so that the electronic filter removes most of its influence on the peak level. Since the width of a blurry disk's peak is relatively narrow, when the camera is looking at a blurry disk, the low pass filter will have a large effect, and the resulting value of PEAKLEVEL will be equivalent to a voltage that is approximately two thirds of the highest video voltage.

DIAMETER1, DIAMETER2, DIAMETER3 are the lengths of the longest horizontal diameters at low, medium and high threshold levels, respectively. The low threshold is fixed at a value (THRESHOLDLOW) just high enough above the noise level to be unaffected by background variations. By definition, the value of DIAMETER1 is taken to be the "actual" diameter of the light disk. The medium threshold is set to greater of PEAKLEVEL minus TDELTANEG or THRESHOLDHIGH. The high threshold is set to PEAKLEVEL plus TDELTAPOS. all three numbers are in units of millimeters and their values are updated sixty times a second. TDELTANEG, TDELTAPOS, and THRESHOLDHIGH are user programmable values.

MINIMUMDIAMETER is the smallest value of DIAMETER1 for the image to be considered a valid pupil. Small values make it hard to distinguish between pupil disk and corneal reflections under certain circumstances. Larger values prevent the use of the instrument on people with small pupils.

DIAMETERDELTA is the largest allowable difference between DIAMETER1 and DIAMETER2 for the image to be considered a valid pupil. The difference between DIAMETER1 and DIAMETER2 is an indication of the blurriness of the camera image. Smaller values of DIAMETERDELTA are more discriminating in rejecting blurry disks but require an actual pupil to be more sharply focussed before it is accepted. This is a user programmable value.

DIAMETERDROP is the smallest allowable difference between the diameter of the pupil disk and the diameter of the corneal reflection (measured at a point just above the highest point on the pupil disk) for the image to be considered a valid pupil. This is a user programmable value.

Thus, the microprocessor 49 computes PUPILPRESENT←(DIAMETER1 ≧MINIMUMDIAMETER) and ((DIAMETER3+DIAMETERDROP) <DIAMETER2)and ((DIAMETER2- +DIAMETERDELTA)≧DIAMETER1).

Figure 8B:
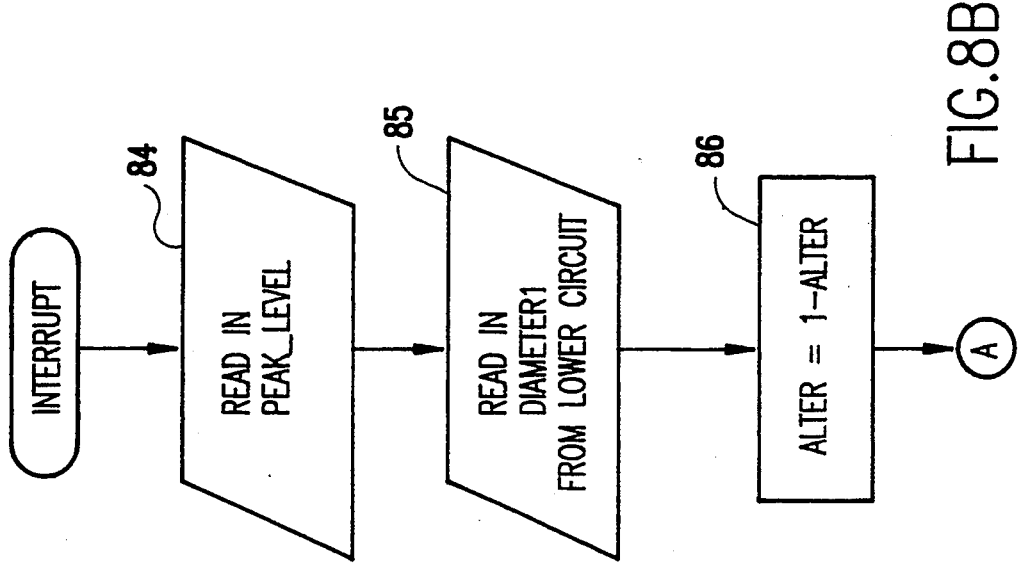
FIG. 8(A–C) is a flow diagram showing the logic of the software subsystem that controls the microprocessor of the system to perform pupil identification.
Figure 8A:
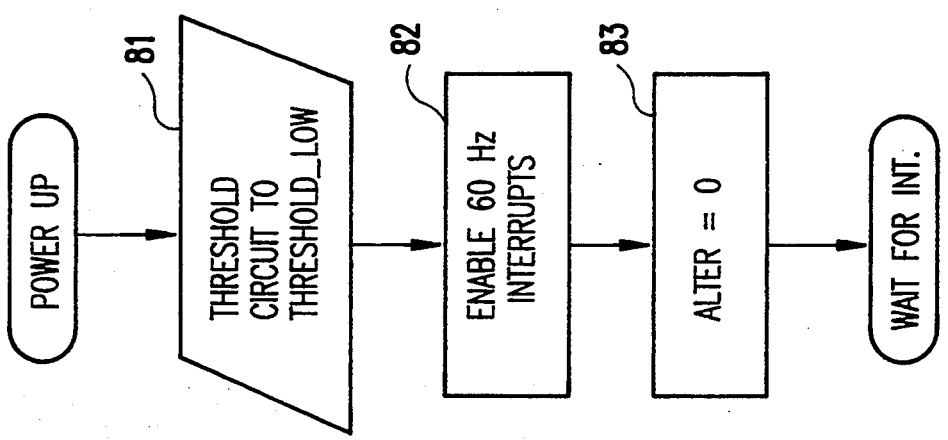
Figure 8C:
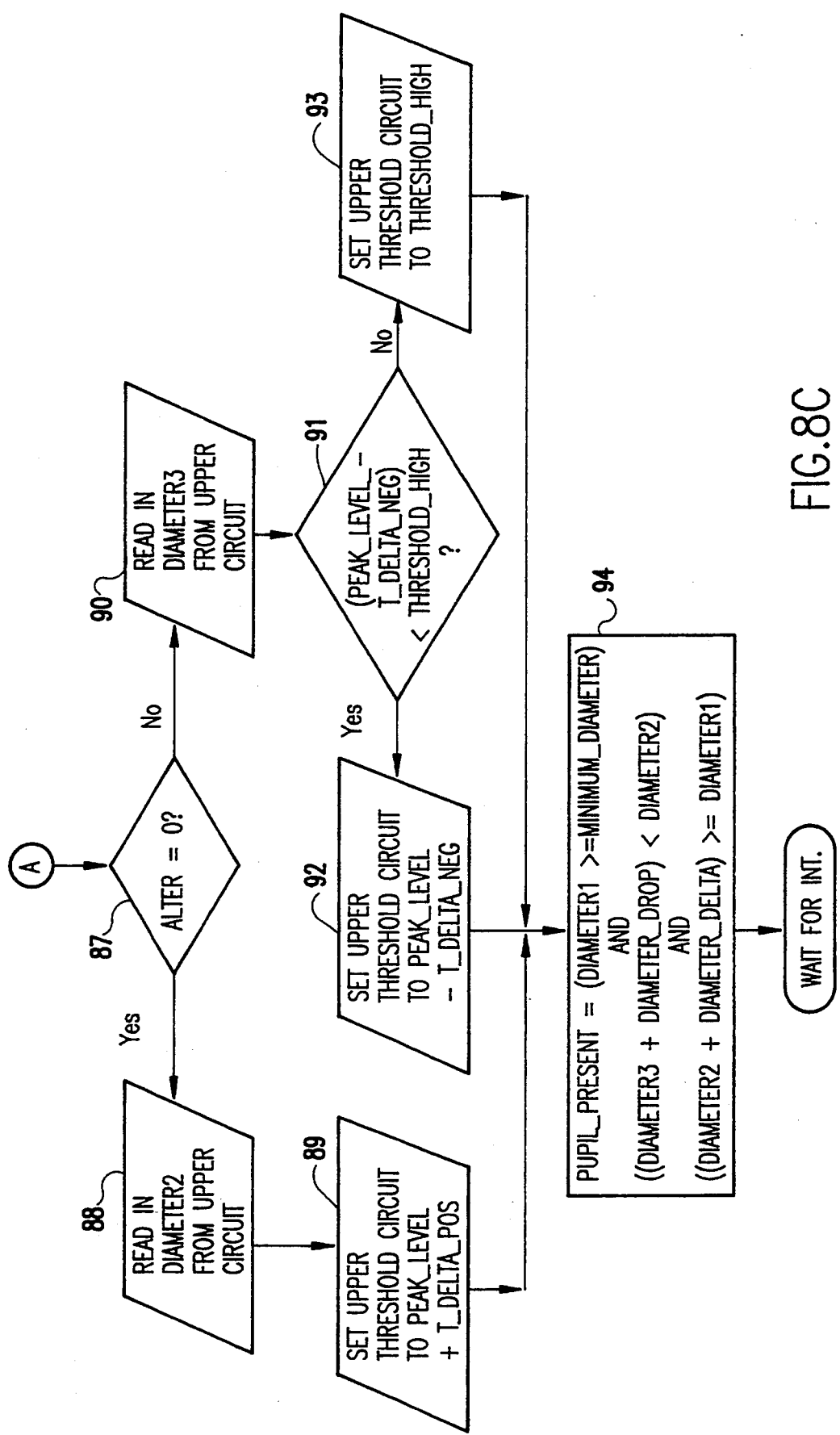

FIG. 8 is a flow diagram showing the logic of the pupil recognition software subsystem. On power up, the threshold circuit is set to THRESHOLDLOW in operation block 81, the 60 Hz interrupts are enabled in function block 82, and "Alter" is set to zero in function block 83. "Alter" is short for alternating and, as will be understood from the following description, is used as a toggle. At this point, the subsystem is initialized and waits for an interrupt.

Upon receiving an interrupt, the PEAKLEVEL value is read in operation block 84, and the DIAMETER1 value is read in operation block 85. Then Alter is subtracted from one on function block 86, and then in decision block 87, Alter is tested to determine if it is zero. Since initially, Alter is set to zero, the result of function block 86 is to change the value of Alter to one. On the next interrupt, the value of Alter is changed back to zero, thus toggling the output of decision block 87 back and forth. When the value of Alter is zero, DIAMETER2 is read in operation block 88, and the upper threshold circuit is set to PEAKLEVEL+TDELTAPOS in operation block 89; otherwise, when the value of Alter is one, DIAMETER3 is read in operation block 90, and a test is made in decision block 91 to determine if PEAKLEVEL minus TDELTANEG is less than THRESHOLDHIGH. If so, the upper threshold is set to PEAKLEVEL minus TDELTANEG in operation block 92; otherwise, it is set to THRESHOLDHIGH in operation block 93. The outputs of operation blocks 89, 92 and 93 are then used by the microprocessor 49 to compute PUPILPRESENT←(- DIAMETER1≧MINIMUMDIAMETER) and ((DIAMETER3+DIAMETERDROP- )<DIAMETER2) and ((DIAMETER2- +DIAMETERDELTA)≧DIAMETER1) in function block 94. The microprocessor then waits for the next interrupt.

The third control subsystem used with the tracking servo loop subsystem according to the preferred embodiment of the invention is the blink detector subsystem. Like the other two software subsystems, it is simple in principle but highly dependent on subtle characteristics of the hardware that make implementation difficult.

Figure 9A:
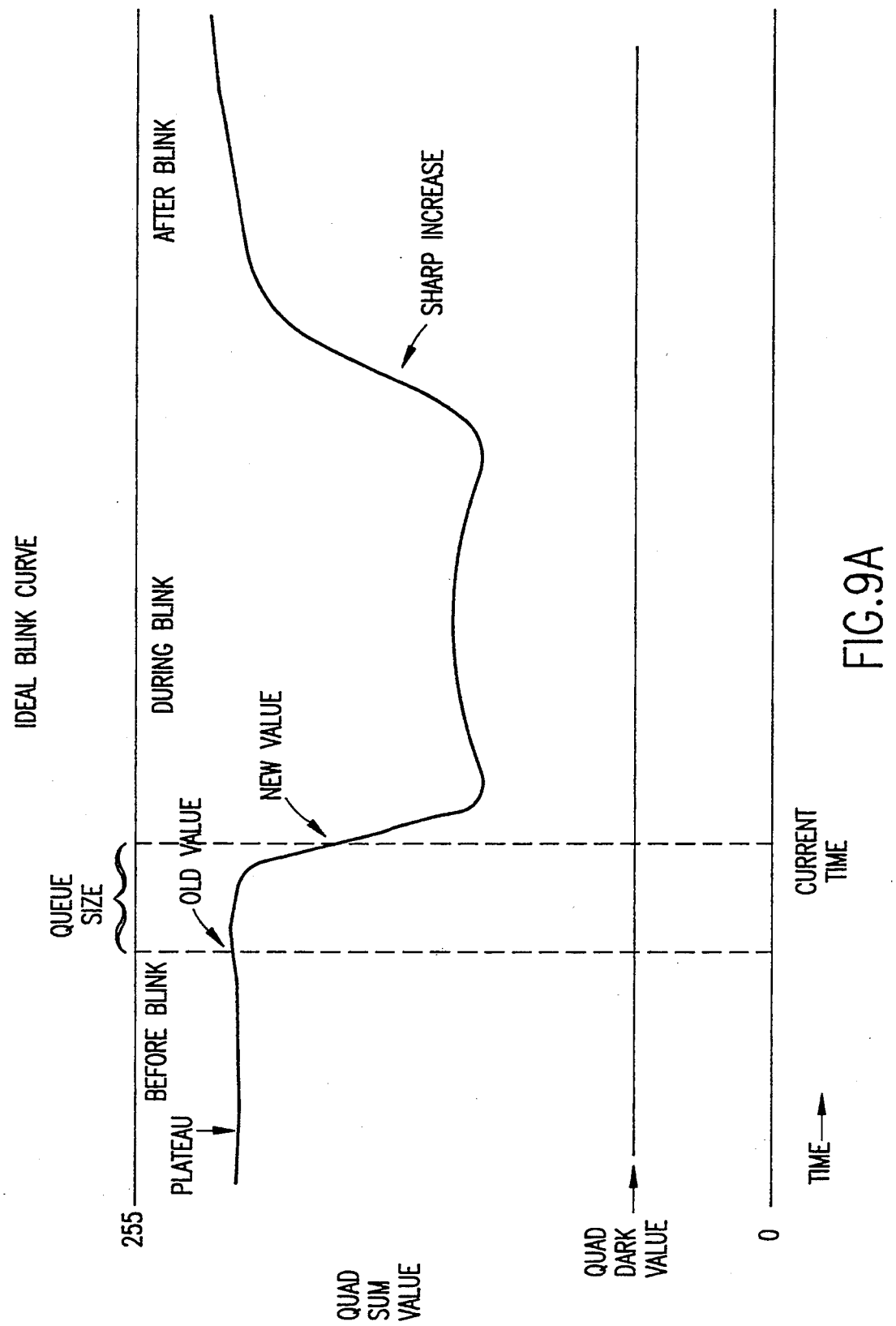
FIG. 9A is a graph showing an ideal blink curve and FIG. 9B is a graph showing a problem blink curve used to illustrate the process of recognizing a blink.
Figure 9B:
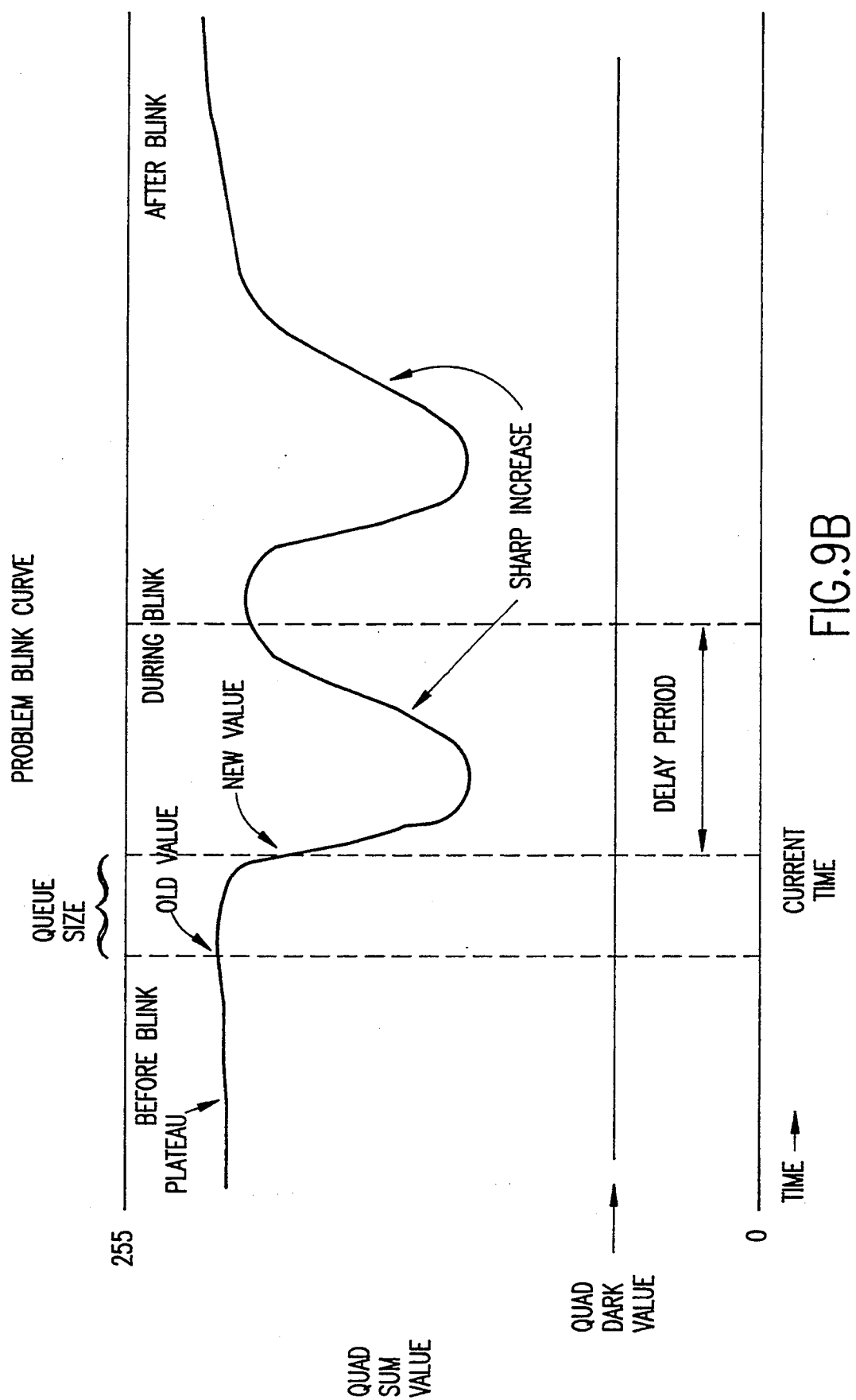

When the servo is tracking properly, the backlighted image of the pupil will remain entirely on the four quadrant detector 23, and the total amount of the light on the quadrant detector will be equal to the product of the area of the pupil by the flux density of the pupil light. These two values will vary over time depending on the subject's angle of gaze and pupil diameter; hence, the quadrant detector sum value will vary over time. However, the rate of change in the quadrant detector sum from these two factors is small compared to the rate of change in the quadrant detector sum value that occurs when the subject blinks. More particularly, as the eyelid cuts across the backlighted pupil, several factors combine to cause a rapid change in the quadrant detector sum, as typified by the quadrant detector sum curve in FIG. 9A. Even in the case where the amount of light falling on the four quadrant detector is very close to the amount when the eye is open, as in the case of very small pupils, there is always a rapid change in the sum signal as the eyelid closes and opens, as shown in FIG. 9B.

Since the plateau level of the sum signal (defined as the signal level when the eye is open) will vary with gaze angle and pupil diameter, setting up a fixed threshold value, above which the eye is open and below which the eye is closed, to detect blinks cannot work. So in order to detect a blink, the blink detector subsystem must detect the rapid decrease in signal directly and, as soon as possible, stop the servo loop subsystem, then look for the rapid increase in sum value that occurs at the end of a blink and restore the servo loop subsystem to normal operation. It should be understood that it is important to disable the servo loop system as early in the blink as possible. When the light reflected from the eyelid falls on the four quadrant detector 23 replacing the light from the pupil, the resulting signal from the four quadrant detector has no relationship to the pupil position and may result in a very large servo error signal. Such a large servo error signal can have the effect of causing the servo loop subsystem to move the tracking mirror away from its current (and correct) location as quickly as possible. On the other hand, when the eyelid has opened, the erroneous quadrant detector difference signal is replaced by a valid pupil signal that will generally have a small servo error.

The challenge in detecting these rapid changes in signal lies in the need for speed. Any algorithm to perform this function will be invoked at each interrupt, i.e., 900 times a second, prohibiting the use of normal floating-point techniques for finding the slope of a curve; e.g., regression line. What is needed is a highly efficient technique that is insensitive to high frequency noise, as a two-point slope calculation would be. Basically, this is done by storing the incoming quadrant detector sum values in a first-in, first-out (FIFO) type queue of length N and comparing the oldest and newest values. If the difference between these two values is greater than, say, 20% of the active signal, then a rapid decrease in signal is occurring, signifying the start of a blink.

The newest value in the queue that was just read from the quadrant detector is called "NewValue" and the oldest value in the queue is called "OldValue". The "DarkValue", which was determined prior to enabling the servos, is an indicator of the noise level on the four quadrant detector. "DelayCount" is the number of clock ticks that must pass after the "SubjectIsBlinking" condition goes true before the conditional "SharpIncrease" can be set true. The value of "DelayCount", which is fixed at compile time, is determined so that the delay time is long enough to get beyond the first sharp increase on the Problem Blink Curve shown in FIG. 9B.

The following code is executed after each servo interrupt:

```
if Subject_Is_Blinking then
    if Delay > 0 then
        Delay ← Delay - 1;
    if (New > Old + Delta*2) and (Delay = 0) then
        Sharp_Increase ← true
    if (New_Value > Blink_Stop_Level) and Sharp_Increase then
        Subject_Is_Blinking ← false
else "Do if subject is not blinking"
    Sharp_Increase ← false
    Delay ← Delay_Count
    Active_Signal ← Old_Value - Dark_Value
    Delta ← Active_signal / 10 "Integer division"
    Blink_Start_Level ← Old_Value - Delta*4
    Blink_Stop_Level ← Old_Value - Delta*2
    if New_Value < Blink_Start_Level then
        Subject_Is_Blinking ← true
```

Figure 10A:
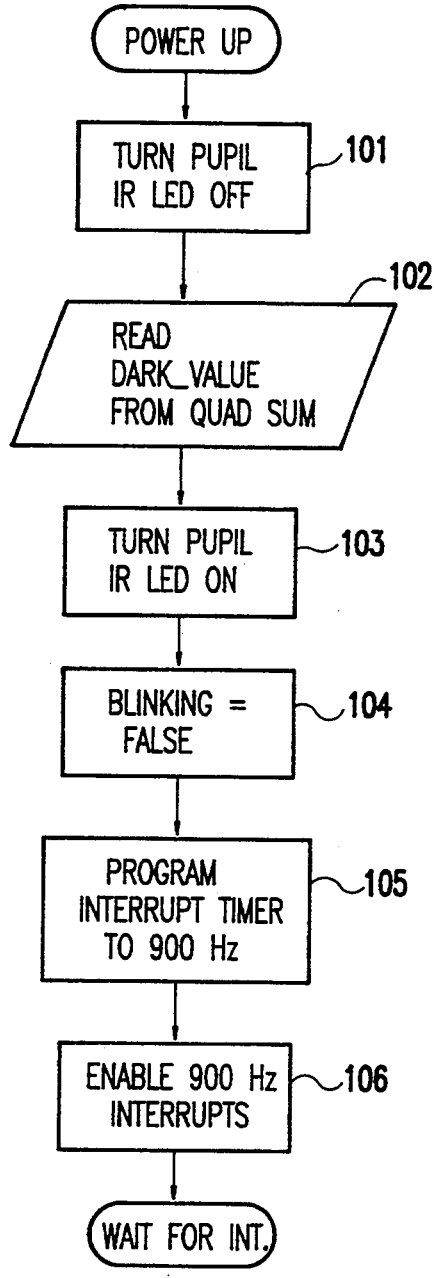
FIG. 10(A-C) is a flow diagram showing the logic of the software subsystem that controls the microprocessor of the system to perform blink detection.
Figure 10C:
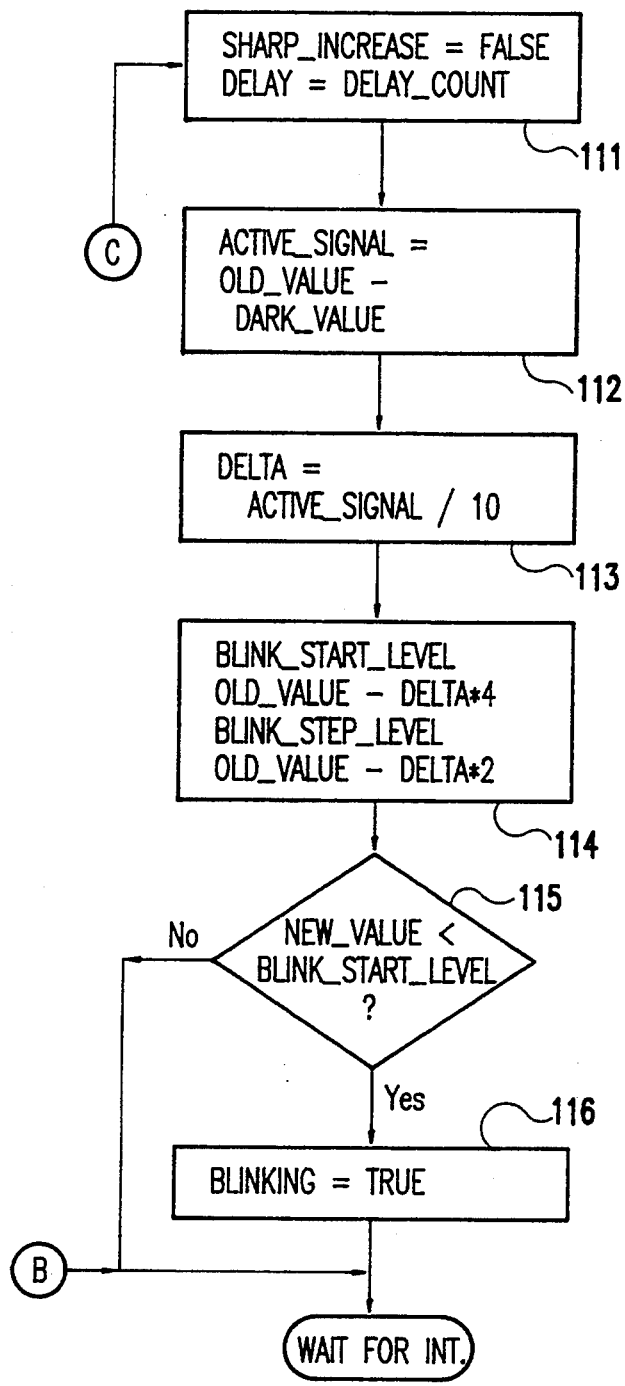
Figure 10B:
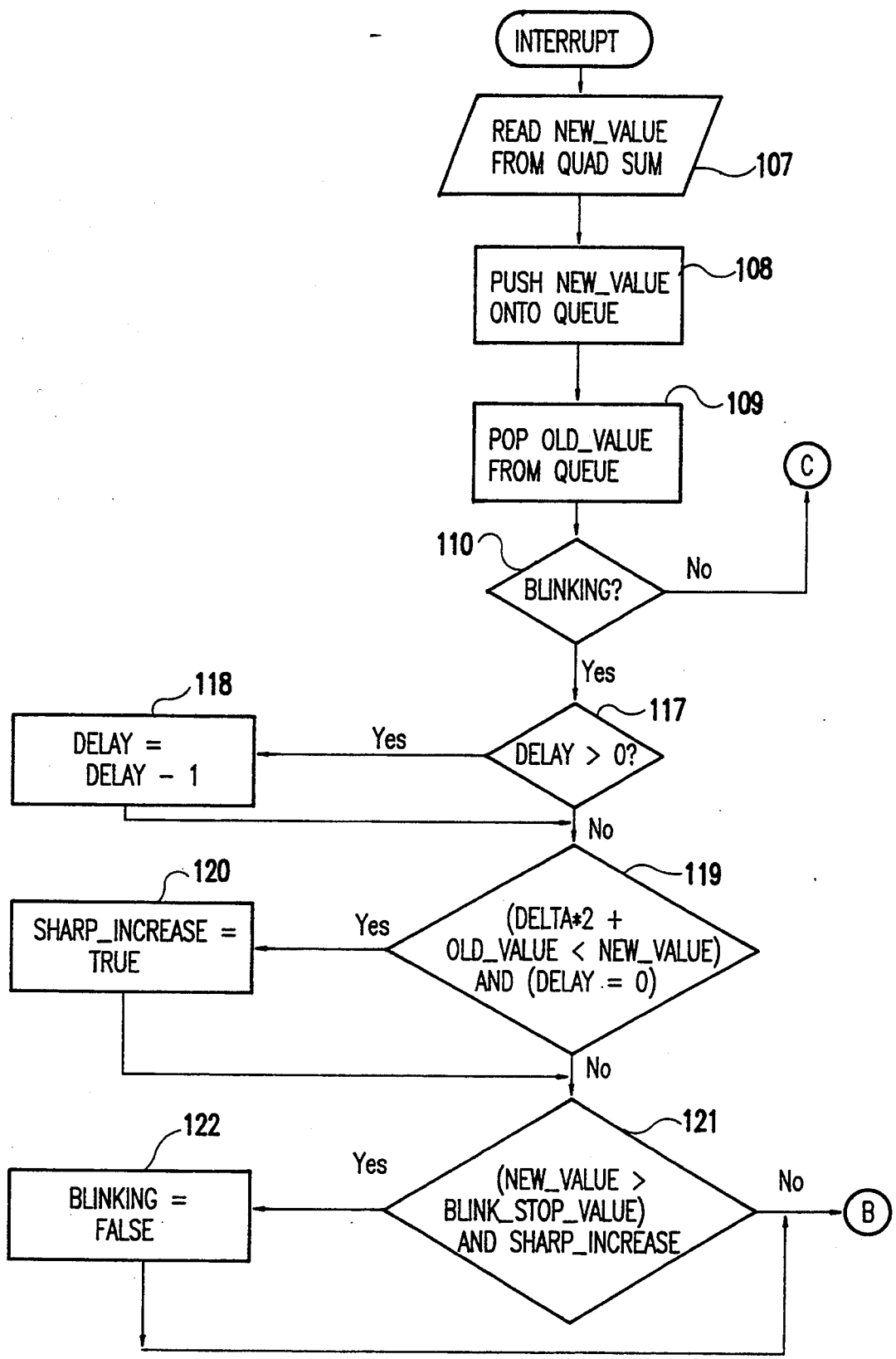

FIG. 10(A-C) is a flow diagram showing the logic of the blink detector subsystem which implements the pseudocode above. At power up, the pupil IR LED 17 is held in the off condition in function block 101, and the DarkValue is read from the quad detector 23 output in operation block 102. The IR LED 17 is then turned on in function block 103, and blinking is set to false in function block 104. The program interrupt timer is set to 900 Hz in function block 105, and the 900 Hz interrupts are enabled in function block 106. The subsystem at this point is initialized and waits for an interrupt.

When an interrupt is received, the NewValue is read from the quad sensor sum output in operation block 107. The NewValue is pushed into the queue in function block 108, and the OldValue is popped out of the queue in function block 109. A test is made in decision block 110 to determine if blinking is detected. If not, SharpIncrease is set to false and the delay is set to DelayCount in function block 111. Next, in function block 112 the ActiveSignal is set to OldValue less the DarkValue measured on initialization. Delta is set to ActiveSignal divided by ten in function block 113, and in function block 114, BlinkStartLevel is set to OldValue minus four times Delta and BlinkStepLevel is set to OldValue minus two times Delta. A test is then made in decision block 115, to determine if NewValue is less than BlinkStartLevel. If so, Blinking is set to true in function block 116 and the subsystem waits for the next interrupt; otherwise, the subsystem simply waits for the next interrupt.

Returning to decision block 110, if Blinking is detected, a further test is made in decision block 117 to determine if the value Delay is greater than zero. If so, the value Delay is decremented by one in function block 118; otherwise, no change is made to the Delay value. A test is then made in decision block 119 to determine if two times Delta plus OldValue is less than NewValue and Delay is equal to zero. If so, SharpIncrease is set to true in function block 120; otherwise, no change is made. Then, in decision block 121, a test is made to determine if NewValue is greater than BlinkStopValue and SharpIncrease is true. If so, Blinking is set to false in function block 122 and the subsystem waits for the next interrupt; otherwise, the subsystem simply waits for the next interrupt.

One last point about the "SubjectIsBlinking" flag. When this condition becomes true, motor movement must be suspended as soon as possible; however, if a motor is traveling at a speed greater than the stop-start speed of that motor and the step commands to the motor are immediately aborted, the motor will still continue to move under mechanical inertia, resulting in the microprocessor losing track of the motor's position. The way around this problem (and an example of the subtle interaction between these three software subsystems) is not to suspend the servo loop during a blink but to set the servo error to zero instead. This achieves the suspension of motor activity but without the possible loss of step integrity that may result without the graceful ramping down of the motors as needed.

It will be appreciated from the foregoing that the eye tracking system according to the invention provides a significant advance in the art of tracking fast eye movements. By illuminating the retina of the eye with a spot of light that is small enough in the pupil plane that it never hits the iris, the light scattered back from the retina and out of the pupil results in an image on the four quadrant detector that looks like a bright disk on a dark background, which is the optimum to furnish error signals to a position measuring system. Although optimum, the signals are not linear. Since the pupil is round, the change in voltage difference between, say, the left and right halves of the four quadrant detector is not linear with the amount of decentering of the pupil and, in fact, depends on the size of the pupil. However, what is important is that when the signals are equal from all four quadrants, by definition the pupil image is centered on the four quadrant detector, and any departures from equality signal that the pupil is not centered on the detector.

In the practice of the invention, both the input light and the light emerging from the pupil are reflected from the tracking mirror. The electronics and tracking program are designed so that if the signals from the four quadrant detector indicate that the pupil image is decentered, say, to the left, then the mirror will rotate, moving the pupil image toward the right. Therefore, the tracking system keeps the pupil image centered on the four quadrant detector. If the eye moves, decentering the pupil, the system moves the tracking mirror just enough to compensate.

The tracking mirror does something else that is quite important. The input light enters the eye in a very small spot that does not hit the iris. Were the light to hit the iris, the image on the four quadrant detector would be an image of the spot hitting the iris so that when the eye moved, the iris moving under the spot would result in the spot not moving with respect to the optical system, so its image would not move on the four quadrant detector. In other words, an eye movement would not be signaled unless the light enters the pupil and misses the iris. Then if the eye moves, the pupil moves, so the input light has to move too, in order to stay centered. That happens in the eye tracking system according the invention because the input light is also reflected from the tracking mirror. Thus, the tracking mirror compensates for eye movements to keep the pupil image centered on the four quadrant detector and at the same time the input light centered on the pupil.

By backlighting the pupil while avoiding illumination of the iris, a simple image of far more contrast than any other system known is achieved, but in order to do so in the presence of any significant movement, the pupil must be accurately tracked. In order to track saccadic movements, the tracking has to have a high sampling rate (or be an analog system with a high frequency response). In the preferred embodiment using stepper motors, the quadrant detector amplifiers have cutoff frequencies well above 1 kHz and their outputs are sampled and the stepper motors that drive the tracking mirror are stepped, 900 times per second. It would also be possible to use the analog outputs of the horizontal and vertical quadrant amplifiers to drive, directly, analog linear actuators, e.g., voice coils, which in mm drive the tracking mirror.

In order for the tracking servo subsystem to work optimally, two special control subsystems have been added. These are the pupil recognition and blink detection subsystems. If there is no blink detection, then when the eye blinks, the system will usually lose tracking because the input illumination will then fall on the eyelid, leaving the tracking servo system in an open loop condition. That is, the tracking mirror can move without causing any change in the error signal. This is because the mirror moves both the input and output paths. If the mirror moves, the spot falling on the eyelid will move, but that movement will be exactly compensated for by the mirror, keeping the image stationary on the four quadrant detector. Thus, the blink detector subsystem locks the tracking servo subsystem in place until the blink is over, on the assumption that the eye will not move so far during the blink that when the eye opens, the spot will miss the pupil. This assumption is true for most cases. The pupil recognition subsystem is needed so that, if the system loses tracking with the result that the light spot does not enter the pupil, loss of tracking can be recognized. Similarly, when a test is started automatically, that is, without needing an operator, the system has to know that a pupil is there before tracking is activated and the test started.

While the invention has been described in terms of a single preferred embodiment, those skilled in the art will recognize that the invention can be practiced with modification within the spirit and scope of the appended claims. For example, in some specialized applications, the software implemented eye tracking subsystem could be implemented in a hardwired circuit which controls analog positioning motors, such as voice coil motors.

Having thus described our invention, what we claim as new and desire to secure by Letters Patent is as follows:

1. An eye tracking system, comprising:
   a source of infrared light;
   optics forming an image of the source of infrared light, said image being smaller than the smallest that pupil of the eye ever becomes;
   a tracking mirror movable about at least one axis and directing the infrared light toward the pupil of the eye, infrared light passing through the pupil of the eye and falling on the eye's retina where it is back-scattered to back light the pupil, and said tracking mirror also reflecting light from the back lighted pupil;
   a beamsplitter intercepting the light from the back lighted pupil and reflected by said tracking mirror;
   a detector positioned to receive light from said beamsplitter, said detector connected to provide a measure of decentering of the light on said detector; and
   a controller connected to receive an output from the detector and generating control signals controlling the rotation of said tracking mirror about said axis to maintain the image of the back lighted pupil centered on the detector.

2. The eye tracking system recited in claim 1 wherein said controller is a computer controlled by a stored program, said computer generating control signal under control of the stored program, the stored program including a tracking servo subsystem which determines decentering of an image of the back lighted pupil on the detector.

3. The eye tracking system recited in claim 2 wherein said tracking mirror is rotatable about two perpendicular axes and said detector is a four quadrant detector providing four outputs, further comprising a circuit interposed between said detector and said computer, said circuit receiving said four outputs and generating outputs representing decentering in at least two perpendicular directions of the image on said detector, said computer controlling the rotation of said tracking mirror about both said two axes to maintain the image of the back lighted pupil centered on the four quadrant detector.

4. The eye tracking system recited in claim 3 wherein said circuit further generates an output which represents the sum of all four outputs of said quadrant detector and includes an analog-to-digital converter providing digitized outputs to said computer.

5. The eye tracking system recited in claim 4 further comprising:
   an image sensor located to receive a projection of the image of the back lighted pupil from said beamsplitter; and a second beamsplitter intercepting the light from said first mentioned beamsplitter and directing light to each of said four quadrant detector and said image sensor.

6. The eye tracking system recited in claim 5 wherein said image sensor is a video camera.

7. The eye tracking system recited in claim 5 wherein said image sensor is a charge coupled device (CCD).

8. The eye tracking system recited in claim 5 wherein said image sensor provides an output to said computer and said stored program further includes a pupil recognition subsystem which detects the presence of an image of the back lighted pupil on the image sensor to enable the tracking servo subsystem.

9. The eye tracking system recited in claim 5 wherein said image sensor provides an output to said computer and said stored program further includes a blink detection subsystem which detects the onset of a blink of the eye and temporarily disables the tracking servo subsystem until the blink is completed.

10. The eye tracking system recited in claim 5 wherein said image sensor provides an output to said computer and said stored program further includes a pupil recognition subsystem which detects the presence of an image of the back lighted pupil on the image sensor to enable the tracking servo subsystem and a blink detection subsystem which detects the onset of a blink of the eye and temporarily disables the tracking servo subsystem until the blink is completed and the pupil is again recognized by the pupil recognition subsystem.

11. An method for tracking a subject's eye movements comprising the steps of:
forming an image of an infrared light source, said image being smaller than the smallest that a pupil of the subject's eye becomes;
directing the image of the infrared light source toward the pupil of the subject's eye so that the infrared light passes through the pupil and falls on the retina of the subject's eye where it is backscattered to back light the pupil;
reflecting light from the back lighted pupil onto a detector using a tracking mirror, said detector providing a measure of decentering of the light on said detector; and
moving said tracking mirror to minimize the decentering of the light on the detector.

12. The method for tracking a subject's eye recited in claim 11 wherein the detector is a four quadrant detector providing four outputs, said method further comprising the steps of:
combining the four outputs to generate outputs representing decentering in at least two perpendicular directions; and
moving said tracking mirror about two perpendicular axes.

13. The method for tracking a subject's eye recited in clam 12 further comprising the step of forming an image of the subject's back lighted pupil on a video image sensor using the tracking mirror to maintain the image of the subject's back lighted pupil centered on the video image sensor.

14. The method for tracking a subject's eye recited in claim 13 further comprising the steps of:
examining an electrical signal from the video image sensor to detect the presence of an image of a back lighted pupil on the video image sensor; and
enabling the moving of the tracking mirror to track the subject's eye.

15. The method for tracking a subject's eye recited in claim 13 further comprising the steps of:
examining an electrical signal from the video image sensor to detect the onset of a blink of the subject's eye; and
temporarily preventing the moving of the tracking mirror until the blink is completed.

16. The method for tracking a subject's eye recited in claim 13 further comprising the steps of:
examining an electrical signal from the video image sensor to detect the presence of an image of a back lighted pupil on the video image sensor;
enabling the moving of the tracking mirror to track the subject's eye;
further examining an electrical signal from the video image sensor during moving of the tracking mirror to detect the onset of a blink of the subject's eye; and
temporarily preventing the moving of the tracking mirror until the blink is completed.

* * * * *